(12) United States Patent
Lee et al.

(10) Patent No.: US 10,307,107 B2
(45) Date of Patent: Jun. 4, 2019

(54) COOPERATIVE SENSING METHOD AND TERMINAL FOR PERFORMING COOPERATIVE SENSING

(71) Applicant: Samsung Electronics Co., Ltd., Suwon-si (KR)

(72) Inventors: Jong Wook Lee, Seongnam-si (KR); Ui Kun Kwon, Hwaseong-si (KR); Seung Keun Yoon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 421 days.

(21) Appl. No.: 14/661,226

(22) Filed: Mar. 18, 2015

(65) Prior Publication Data

US 2016/0106371 A1 Apr. 21, 2016

(30) Foreign Application Priority Data

Oct. 16, 2014 (KR) ......................... 10-2014-0139668

(51) Int. Cl.
| | | |
|---|---|---|
| A61B 5/00 | (2006.01) | |
| H04W 4/70 | (2018.01) | |
| H04W 4/00 | (2018.01) | |
| A61B 5/024 | (2006.01) | |
| A61B 5/11 | (2006.01) | |
| H04W 4/80 | (2018.01) | |

(52) U.S. Cl.
CPC .......... *A61B 5/7221* (2013.01); *A61B 5/6898* (2013.01); *H04W 4/005* (2013.01); *H04W 4/70* (2018.02); *A61B 5/02416* (2013.01); *A61B 5/1112* (2013.01); *A61B 2560/0214* (2013.01); *A61B 2560/0223* (2013.01); *H04W 4/008* (2013.01); *H04W 4/80* (2018.02)

(58) Field of Classification Search
USPC ......................................................... 702/182
See application file for complete search history.

(56) References Cited

U.S. PATENT DOCUMENTS

| | | | |
|---|---|---|---|
| 8,591,455 B2 | 11/2013 | Mensinger et al. | |
| 2014/0066095 A1* | 3/2014 | Huang ................. | G01S 5/0027 |
| | | | 455/456.2 |
| 2014/0237028 A1* | 8/2014 | Messenger ............ | G06Q 30/02 |
| | | | 709/203 |

FOREIGN PATENT DOCUMENTS

| | | | |
|---|---|---|---|
| KR | 10-2006-0069147 A | | 6/2006 |
| KR | 10-2007-0025037 A | | 3/2007 |
| KR | 10-2009-0061153 A | | 6/2009 |
| KR | 10-2010-0124591 A | | 11/2010 |
| KR | 1020090043682 | * | 11/2010 |
| KR | 10-2011-0091753 A | | 8/2011 |
| KR | 10-2011-0120372 A | | 11/2011 |
| KR | 10-1201604 B1 | | 11/2012 |
| KR | 10-2014-0014640 A | | 2/2014 |

* cited by examiner

*Primary Examiner* — Roy Y Yi
(74) *Attorney, Agent, or Firm* — NSIP Law

(57) ABSTRACT

A cooperative sensing method of a terminal, the method including transmitting a request to a cooperative terminal connected with the terminal, to verify a sensing performance capability of the cooperative terminal, receiving, from the cooperative terminal, first capability information generated in response to the request, and selecting, by the terminal, a sensing terminal based on the first capability information and second capability information generated by verifying a sensing performance capability of the terminal.

20 Claims, 9 Drawing Sheets

COOPERATIVE SENSING METHOD AND TERMINAL FOR PERFORMING COOPERATIVE SENSING

CROSS-REFERENCE TO RELATED APPLICATION(S)

This application claims the benefit under 35 USC 119(a) of Korean Patent Application No. 10-2014-0139668, filed on Oct. 16, 2014, in the Korean Intellectual Property Office, the entire disclosure of which is incorporated herein by reference for all purposes.

BACKGROUND

1. Field

The following description relates to a cooperative sensing method and a terminal for performing cooperative sensing.

2. Description of Related Art

Lately, multi-type sensors are being mounted on a personal mobile device based on developing hardware and software algorithms. For example, most recent types of smartphones include a global positioning system (GPS) sensor, an acceleration sensor, and a Gyro sensor, and most recent types of wearable devices include a photoplethysmography (PPG) sensor. The smartphone or the wearable device receives an input from a user, and performs a predetermined function in response to the input from the user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a cooperative sensing method of a terminal, the method including transmitting a request to at least one cooperative terminal connected with the terminal, verifying a sensing performance capability of the terminal to generate second capability information, receiving, from the cooperative terminal, first capability information generated in response to the request, and selecting a sensing terminal to perform sensing, using at least one of the first capability information and the second capability information.

The transmitting may include requesting the cooperative terminal to perform pilot sensing to verify a sensing accuracy of the cooperative terminal, and the verifying may include performing pilot sensing to verify a sensing accuracy of the terminal.

The selecting may include selecting, by the terminal, the sensing terminal using status information associated with the terminal and the cooperation terminal.

The status information may include at least one of information on sensors included in the terminal and the cooperative terminal, battery information of the terminal and the cooperative terminal, an amount of power used for sensing performed by each of the terminal and the cooperative terminal, and user preference information associated with the sensing terminal.

The selecting may include verifying sensing accuracies of the terminal and the cooperative terminal based on the first capability information and the second capability information, and selecting, by the terminal, the sensing terminal based on battery information of the terminal and the cooperative terminal when a difference between the verified sensing accuracies is within a reference range.

The selecting may include verifying sensing accuracies of the terminal and the cooperative terminal based on the first capability information and the second capability information, and selecting, by the terminal, the sensing terminal based on individual preference information associated with the sensing terminal when a difference between the verified sensing accuracies is within a reference range.

The cooperative sensing method may further include transmitting a sensing request to the cooperative terminal to perform the sensing when the cooperative terminal is selected as the sensing terminal, receiving, from the cooperative terminal, sensing information acquired by performing the sensing, and outputting the sensing information based on at least one of a visual scheme, an auditory scheme, and a tactile scheme.

The cooperative sensing method may further include selecting, from among a plurality of neighboring terminals connected with the terminal, the cooperative terminal to perform the pilot sensing based on status information associated with the neighboring terminals.

The status information may include at least one of information on a sensor included in each of the plurality of neighboring terminals, battery information for each of the neighboring terminals, and an amount of power used for pilot sensing performed by each of the neighboring terminals.

The sensing accuracy is determined based on an environment for each of the terminal and the cooperative terminal.

In another general aspect, there is also provided a cooperative sensing method of a cooperative terminal, the method including receiving a request from a terminal connected with the cooperative terminal, verifying the sensing performance capability of the cooperative terminal in response to the request and generating second capability information, and transmitting first capability information to the terminal, wherein the terminal selects a sensing terminal for performing sensing, based on the first capability information and the second capability information.

The verifying may include performing pilot sensing to verify a sensing accuracy of the cooperative terminal.

The sensing terminal is selected by the terminal by additionally using status information associated with the terminal and the cooperative terminal.

The status information may include at least one of information on sensors included in the terminal and the cooperative terminal, battery information associated with the terminal and the cooperative terminal, an amount of power used for sensing performed by each of the terminal and the cooperative terminal, and user preference information with respect to the sensing terminal.

In still another general aspect, there is also provided a terminal for performing cooperative sensing, the terminal including a transmitter configured to transmit a request to at least one cooperative terminal connected with the terminal, a verifier configured to verify a sensing performance capability of the terminal and generate second capability information, a receiver configured to receive, from the cooperative terminal, first capability information generated in response to the request, and a controller configured to select a sensing terminal to perform sensing, using at least one of the first capability information and the second capability information.

The transmitter is configured to request the cooperative terminal to perform pilot sensing to verify a sensing accuracy of the cooperative terminal, and the verifier is configured to perform pilot sensing to verify a sensing accuracy of the terminal.

The controller is configured to select the sensing terminal by additionally using status information associated with the terminal and the cooperative terminal.

The status information may include at least one of information on sensors included in the terminal and the cooperative terminal, battery information associated with the terminal and the cooperative terminal, an amount of power used for sensing performed by each of the terminal and the cooperative terminal, and user preference information associated with the sensing terminal.

The controller is configured to verify sensing accuracies of the terminal and the cooperative terminal based on the first capability information and the second capability information, and configured to select the sensing terminal based on battery information of the terminal and the cooperative terminal when a difference between the verified sensing accuracies is within a reference range.

The controller is configured to verify sensing accuracies of the terminal and the cooperative terminal based on the first capability information and the second capability information, and configured to select the sensing terminal based on user preference information with respect to the sensing terminal when a difference between the verified sensing accuracies is within a reference range.

When the cooperative terminal is selected as the sensing terminal, the transmitter is configured to transmit a sensing request to the cooperative terminal to perform sensing, the receiver is configured to receive sensing information acquired by performing the sensing from the cooperative terminal, and the terminal may further include an output unit configured to output the sensing information based on at least one of a visual scheme, an auditory scheme, and a tactile scheme.

The terminal may further include a cooperative terminal selector configured to select the cooperative terminal for performing the pilot sensing, from a plurality of neighboring terminals based on status information associated with the neighboring terminals.

The status information may include at least one of information on a sensor included in each of the plurality of neighboring terminals, battery information for each of the neighboring terminals, and an amount of power used for the pilot sensing performed by each of the neighboring terminals.

In yet another general aspect, there is also provided a cooperative terminal for performing cooperative sensing, the cooperative terminal including a receiver configured to receive a request from a terminal connected with the cooperative terminal to verify a sensing performance capability of the cooperative terminal, a verifier configured to verify the sensing performance capability of the cooperative terminal in response to the request, and a transmitter configured to transmit, to the terminal, first capability information generated based on a result of the verifying, wherein the terminal is configured to select a sensing terminal to perform sensing, using at least one of the first capability information and second capability information generated by verifying a sensing performance capability of the terminal.

Other features and aspects will be apparent from the following detailed description, the drawings, and the claims.

Figure 1:
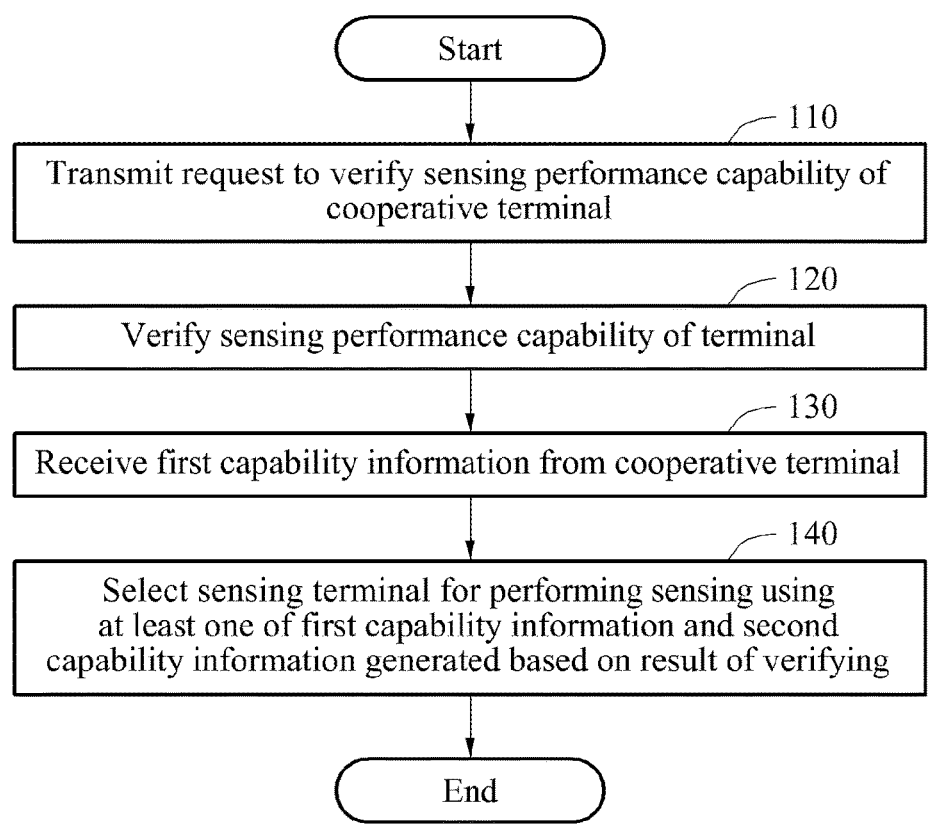
FIG. 1 is a flowchart illustrating an example of a cooperative sensing method of a terminal.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings is exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Like reference numerals in the drawings denote like elements, and redundant descriptions of like elements will be omitted herein. When it is determined a detailed description of a related known function or configuration they may make the purpose of the present disclosure unnecessarily ambiguous in describing the present disclosure, the detailed description will be omitted herein.

FIG. 1 is a flowchart illustrating an example of a cooperative sensing method of a terminal.

The cooperative sensing method is performed by the terminal. In this example, the terminal includes a mobile terminal. The mobile terminal includes, for example, a smartphone, a tablet personal computer (PC), a laptop computer, and a wearable device.

In operation 110, the terminal transmits a request to at least one cooperative terminal connected with the terminal, to verify a sensing performance capability of the cooperative terminal. In response to the request, the cooperative terminal transmits information to the terminal indicating whether a sensing is to be performed.

The terminal receives an execution request for a predetermined sensing function from a user. In response to the execution request received from the user, the terminal verifies whether the cooperative terminal is capable of performing the predetermined sensing function. By verifying a sensing performance capability of the cooperative terminal, the capability of the cooperative terminal for performing the predetermined function is verified. Also, when the cooperative terminal is capable of performing the predetermined sensing function, a sensing accuracy of the cooperative terminal with respect to the predetermined sensing function is verified by verifying the sensing performance capability.

In an example, the terminal requests a pilot sensing from the cooperative terminal to verify the sensing accuracy of the cooperative terminal with respect to the predetermined sensing function. In response to a reception of the request for verifying the sensing performance capability, the cooperative terminal verifies whether the pilot sensing is to be performed. When the cooperative terminal is incapable of performing the pilot sensing, a message indicating that the pilot sensing is not performed is transmitted to the terminal in response to the request.

The terminal and the at least one cooperative terminal include a communication interface, and form a network using the communication interface. The communication interface includes a wireless Internet interface and a local communication interface. For example, the wireless Internet interface includes a wireless local area network (WLAN), a wireless fidelity (WiFi) direct, a digital living network alliance (DLNA), a wireless broadband (WiBro), a world interoperability for microwave access (WiMAX), and a high speed downlink packet access (HSDPA), and. Meanwhile, the local communication interface includes for example, a Bluetooth™ module, a radio frequency identification (RFID) tag, an infrared data association (IrDA), an ultra wideband (UWB), a ZigBee, a near field communication (NFC), and a wireless body area network (WBAN). Also, the communication interface indicates any interface, for example, a wired interface, for communicating with an external source.

For example, the terminal requests the cooperative terminal connected with the terminal to perform the pilot sensing. The cooperative terminal performs the pilot sensing during a predetermined period of time, for example, 30 seconds. As described below, the terminal receives a result of the pilot sensing performed by the cooperative terminal, and verifies the sensing accuracy of the cooperative terminal based on the received result. However, it is to be noted, this is only one example of the verification process and therefore other verification processes may be used.

In operation 120, the terminal verifies a sensing performance capability of the terminal. The terminal transmits the request to the cooperative terminal, and then verifies the sensing performance capability of the terminal. The terminal needs to verify whether the terminal is capable of performing the predetermined sensing function. Whether the terminal is capable of performing the predetermined sensing function is verified by verifying the sensing performance capability of the terminal. Also, when the cooperative terminal is capable of performing a sensing function, a sensing accuracy of the terminal with respect to the predetermined sensing function is verified by verifying the sensing performance capability of the cooperative terminal.

In an example, the terminal performs the pilot sensing to verify the sensing accuracy of the terminal. The terminal performs the pilot sensing to verify the sensing accuracy of the terminal with respect to the predetermined sensing function. The terminal performs the pilot sensing during a predetermined period of time, for example, 30 seconds. The terminal acquires pilot sensing information by performing the pilot sensing. The terminal verifies the sensing accuracy of the terminal based on the pilot sensing information.

The sensing accuracy of the cooperative terminal depends on an environment of the cooperative terminal. Similarly, the sensing accuracy of the terminal depends on an environment of the terminal. For example, in comparison to a case in which a terminal including a global positioning system (GPS) sensor is disposed in an indoor region, to a case in which the terminal is disposed in an outdoor region, location information on the terminal is more accurately acquired when the terminal is disposed in the outdoor region.

In operation 130, from the cooperative terminal, the terminal receives first capability information generated in response to the request for verifying the sensing performance capability. The first capability information includes information indicating whether the cooperative terminal is capable of performing the predetermined sensing function. For example, when the cooperative terminal is incapable of performing the predetermined sensing function, a message indicating the predetermined sensing function is not performed is transmitted to the terminal. Also, when the cooperative terminal is capable of performing the predetermined sensing function, the first capability information includes the pilot sensing information indicating a result of the pilot sensing. The pilot sensing information includes information acquired by the cooperative terminal using a sensor during a predetermined period of time.

In operation 140, the terminal selects a sensing terminal to perform sensing using at least one of the first capability information and second capability information generated by verifying the sensing performance capability of the terminal. The terminal verifies whether the cooperative terminal is capable of performing the predetermined sensing function, using at least one of the first capability information and the second capability information. In this example, the cooperative terminal differs from the terminal. Alternatively, the terminal determines whether the terminal is appropriate to perform the predetermined sensing function based on the first capability information and the second capability information.

As an example, when the cooperative terminal provides a notification to the terminal indicating that the cooperative terminal is incapable of performing the predetermined sensing function, the terminal selects the terminal as the sensing terminal. Alternatively, when the terminal determines that the terminal is incapable of performing the predetermined sensing function, the cooperative terminal is selected as the sensing terminal.

When both terminal and cooperative terminal are capable of performing the predetermined sensing function, the terminal selects a device for performing the sensing more accurately from between the terminal and the cooperative terminal based on the first capability information and the second capability information. For example, to sense a heart rate of a user, the terminal uses a camera, and the cooperative terminal uses a photoplethysmography (PPG) sensor. When a brightness of the environment or situation is relatively low, the terminal inaccurately senses the heart rate of the user using the camera. In this example, a pilot sensing result of the cooperative terminal is more accurate than a pilot sensing result of the terminal. The terminal compares the pilot sensing result of the terminal to the pilot sensing result of the cooperative terminal. Based on a result of the comparing, the terminal selects the cooperative terminal providing the pilot sensing result more accurately, as the sensing terminal to sense the heart rate of the user.

In an example, the terminal determines the sensing terminal by additionally using status information associated with the terminal and the cooperative terminal. The sensing performance capability of the terminal is similar to the sensing performance capability of the cooperative terminal. For example, the pilot sensing result of the terminal is similar to the pilot sensing result of the cooperative terminal. As described above, depending on a situation, the heart rate of the user acquired by the terminal using the camera is similar to a heart rate of the user acquired by the cooperative terminal using the PPG sensor. In an example, when the pilot sensing result of the terminal is similar to the pilot sensing result of the cooperative terminal, it is difficult for the terminal to select the sensing terminal based only on the sensing performance abilities of the terminal and the cooperative terminal.

Therefore, the terminal selects the sensing terminal by additionally using at least one of information on sensors included in the terminal and the cooperative terminal, battery information associated with the terminal and the cooperative terminal, and power for use in the sensing performed by the terminal and the cooperative terminal, and user preference information with respect to the sensing terminal.

In an example, the terminal verifies sensing accuracies of the terminal and the cooperative terminal with respect to the predetermined sensing function based on the first capability information and the second capability information. Also, when a difference between the verified sensing accuracies is within a reference range, the terminal selects the sensing terminal based on the battery information associated with the terminal and the cooperative terminal. For example, the terminal verifies the sensing performance capability of the terminal and sensing performance abilities of cooperative terminals, for example, cooperative terminals A and B. When the terminal and the plurality of cooperative terminals are capable of performing the predetermined sensing function, the terminal verifies sensing accuracies of the terminal and the plurality of cooperative terminals with respect to the predetermined sensing function. As described above, the sensing accuracy is acquired by performing the pilot sensing. The terminal compares the sensing accuracies of the terminal and the plurality of cooperative terminals. Also, the terminal compares sensing accuracies of the cooperative terminal A and the cooperative terminal B. The terminal determines that the sensing accuracies of the terminal and the plurality of cooperative terminals are similar. Based on a result of the determining, the terminal verifies a battery level, a battery capacity, or power or energy stored in a battery of the cooperative terminal. In this example, the battery level indicates a ratio between a total amount of power to be stored in the battery and an amount of power stored in the battery. The terminal selects the sensing terminal based on the battery information associated with the terminal and the cooperative terminal.

As another example, when the pilot sensing result indicates that the sensing accuracies of the terminal and the cooperative terminal with respect to the predetermined sensing function are similar to one another, the terminal selects the sensing terminal based on an amount of energy stored in a battery of each of the terminal and the cooperative terminal. A device storing a greater amount of energy is selected as the sensing terminal.

As still another example, when the pilot sensing result indicates that the sensing accuracies of the terminal and the cooperative terminal with respect to the predetermined sensing function are similar to one another, the terminal selects the sensing terminal based on battery levels of the terminal and the cooperative terminal. The terminal verifies whether the battery levels are less than a preset threshold level. Based on a result of the verifying, a device having a battery level less than the threshold level may not be selected as the sensing terminal. Also, when the battery levels of the terminal and the cooperative terminal are greater than or equal to the threshold level, the terminal selects the sensing terminal based on an amount of power to be used for the sensing performed by each of the terminal and the cooperative terminal. Despite the similarity between the battery levels of the terminal and the cooperative terminal, the amounts of power stored in the batteries of the terminal and the cooperative terminal may differ. By using the amounts of power used for the sensing performed by the terminal and the cooperative terminal, the terminal prevents a device from storing a less amount of power from being discharged.

In an example, the terminal verifies the sensing accuracies of the terminal and the cooperative terminal with respect to the predetermined sensing function based on the first capability information and the second capability information. Also, when the difference between the verified sensing accuracies is within a reference range, the terminal selects the sensing terminal based on the user preference information with respect to the sensing terminal. When the pilot sensing result indicates that the sensing accuracies of the terminal and the cooperative terminal are similar to one another, the terminal uses the user preference information with respect to the sensing terminal.

For example, the terminal and the cooperative terminal sense a moving distance of the user. The user sets a device for sensing the moving distance between the terminal and the cooperative terminal in advance. A priority of the device for sensing the moving distance between the terminal and the cooperative terminal is set by the user. When the pilot sensing results of the terminal and the cooperative terminal indicate that the sensing accuracies of the terminal and the cooperative terminal are similar, a device having a higher priority is selected as the sensing terminal for sensing the moving distance of the user.

When the terminal and the cooperative terminal are capable of sensing the moving distance of the user in response to the execution request for the predetermined sensing function from the user, the types of sensors driven by the terminal and the cooperative terminal may differ. Among sensors for sensing the moving distance, the user may assign a priority to any one of the sensors. When the pilot sensing result indicates that a measured value of a sensor included in the terminal is similar to a measured value of a sensor included in the cooperative terminal, the terminal selects a device including the sensor to which the priority is assigned, as the sensing terminal.

Also, the terminal provides, to the user, a list of sensors to be driven in a process of measuring the moving distance. As described above, the terminal acquires information on the sensor included in the cooperative terminal. The terminal verifies the types of sensors included in the cooperative terminal. The user selects a sensor to be driven in the process of measuring the moving distance based on the list of the sensors. Through this, a sensor selected by the user or a sensor having a type preferred by the user is selected.

In an example, when the cooperative terminal is selected as the sensing terminal, the terminal transmits the sensing request to the cooperative terminal to perform the sensing. Sensing information acquired through the sensing performed by the cooperative terminal is received by the terminal from the cooperative terminal. The terminal outputs the sensing information based on one of a visual scheme, an auditory scheme, and a tactile scheme. For example, the terminal displays the sensing information on a display, and outputs the sensing information using a speaker. Also, the terminal may provide the sensing information to the user using a vibration. The user may verify the sensing information based on the visual scheme, the auditory scheme, and the tactile scheme.

In an example, the terminal selects a cooperative terminal for performing the pilot sensing from among neighboring terminals connected with the terminal, based on status information associated with the neighboring terminals. In this example, the status information is at least one of information on a sensor included in each of the neighboring terminals, battery information for each of the neighboring terminals, and an amount of power used for the pilot sensing performed by each of the neighboring terminals using the sensor.

The battery information for each of the neighboring terminals include a battery level, a battery capacity, or an amount of power or energy stored in a battery of each of the neighboring batteries.

The terminal acquires status information for each of the plurality of neighboring terminals using the communication interface. The terminal verifies a type of sensor, for example, a GPS sensor, an acceleration sensor, and a Gyro sensor, included in each of the neighboring terminals. In response to a reception of an input for executing a moving distance sensing function from the user, the terminal identifies neighboring terminals including a sensor to sense the moving distance. In one example, when the sensor to sense the moving distance is not included in each of the neighboring terminals, the terminal does not select the neighboring terminals as the cooperative terminal.

The terminal selects the cooperative terminal from among neighboring terminals based on battery information for each of the neighboring terminals. For example, the terminal selects a neighboring terminal having a battery storing a relatively large amount of energy, as the cooperative terminal. Additionally, from among the neighboring terminals, the terminal selects a neighboring terminal having a battery level greater than or equal to the threshold level, as the cooperative terminal. Conversely, the terminal does not select a neighboring terminal having a battery level less than the threshold level as the cooperative terminal. Also, the terminal selects the cooperative terminal from among the plurality of neighboring terminals based on the amount of power used for the pilot sensing performed by each of the neighboring terminals.

Figure 2:
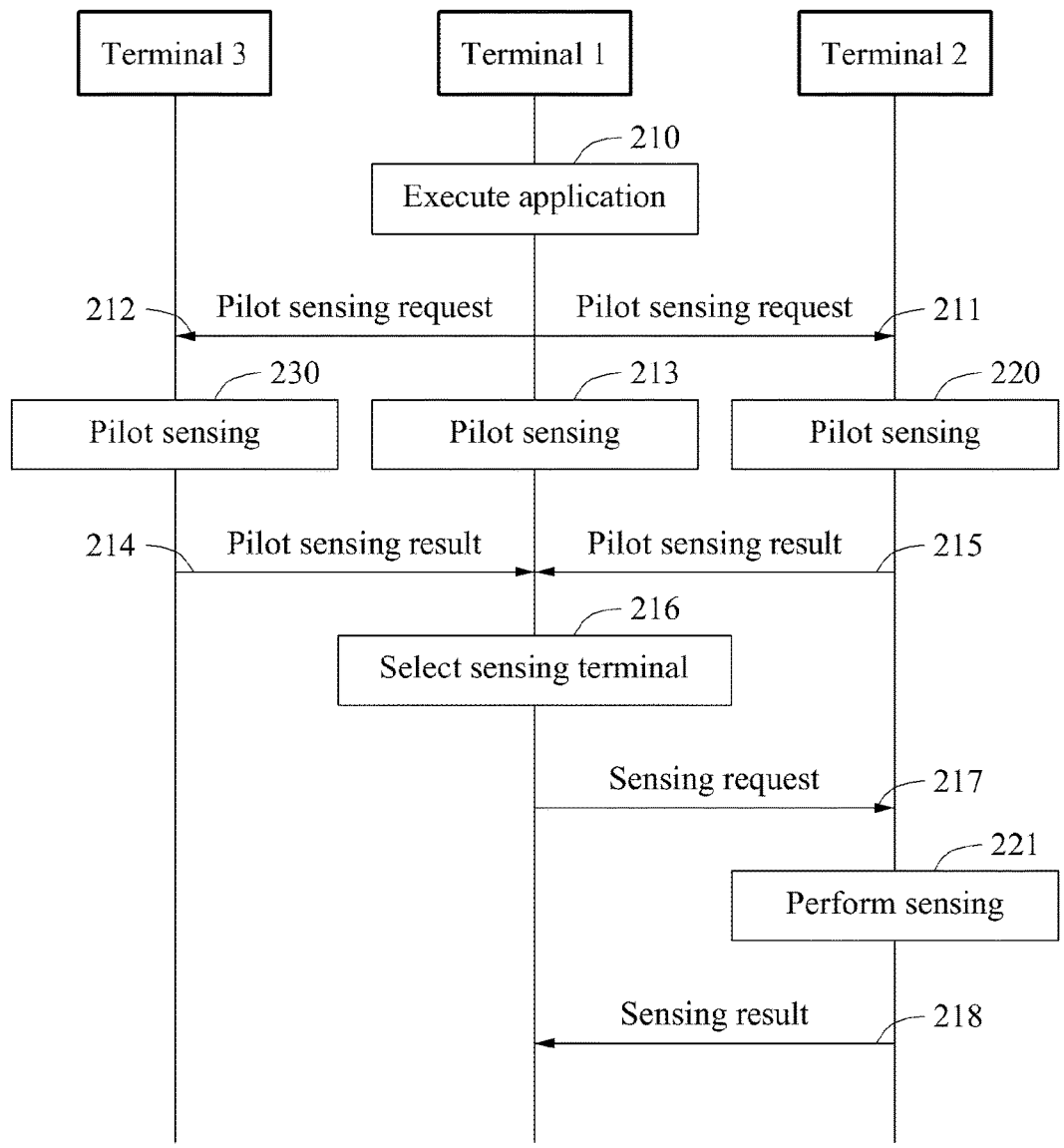
FIG. 2 is a diagram illustrating an example of a cooperative sensing method performed by terminals in a network.

FIG. 2 is a diagram illustrating an example of a cooperative sensing method performed by terminals in a network.

The network includes terminals, and the terminals are connected to one another. For example FIG. 2 illustrates three terminals connected to one another. In operation 210, a terminal 1 receives an execution request for a predetermined sensing function from a user, and executes an application to perform the predetermined sensing function. As an example, the predetermined sensing function includes, for example, a function to measure calories used by the user, a function to measure a moving distance of the user, a function to measure a heart rate of the user, and a function to measure an electric conductivity of a skin of the user. However, the functions are not limited thereto and other sensing functions may be included such as sensing a heartbeat, and blood pressure.

Although not shown in FIG. 2, the terminal 1 may request the terminals paired with the terminal 1, to provide status information for each of the terminals in response to an execution of the application. In this example, the status information includes, for example, information on a sensor included in each of the terminals, battery information for each of the terminals, and power for use in a sensing performed by each of the terminals. A terminal 2 transmits status information on the terminal 2 to the terminal 1, and a terminal 3 transits status information on the terminal 3 to the terminal 1. The terminal 1 receives the status information for each of the plurality of terminals paired with the terminal 1, and verifies the received status information.

Although not shown in FIG. 2, the terminal 1 selects terminals to perform pilot sensing. The terminal 1 selects a terminal to perform the pilot sensing based on the status information for each of the terminals. For example, the terminal 1 receives an input for executing a function to measure the moving distance of the user, from the user. The terminal 1 executes an application to measure the moving distance, and receives the status information from the plurality of terminals paired with the terminal. The terminal 1 selects a terminal capable of performing a pilot sensing to measure the moving distance, from among the terminals based on the status information. A GPS sensor or an acceleration sensor is used to measure the moving distance but is not limited thereto. That is, other types of sensors may be used to measure the moving distance such as a gyrosensor. Thus, in one example, the terminal 1 does not select a terminal lacking the GPS sensor and the acceleration sensor as the terminal capable of performing the pilot sensing.

The terminal 1 selects the terminal 2 and the terminal 3 as the terminal for performing the pilot sensing from among the terminals. In response to the execution of the application, the terminal 1 transmits a pilot sensing request to the terminal 2 in operation 211, and transmits a pilot sensing request to the terminal 3 in operation 212. In response to the pilot sensing request, the terminal 2 performs the pilot sensing in operation 220. In response to the pilot sensing request, the terminal 3 performs the pilot sensing in operation 230. In operation 213, the terminal 1 performs the pilot sensing in response to the transmitting of the pilot sensing request. In operation 215, the terminal 1 receives a result of the pilot sensing performed by the terminal 2 from the terminal 2. In operation 214, the terminal 1 receives a result of the pilot sensing performed by the terminal 3 from the terminal 3.

Based on the results of the pilot sensing, the terminal 1 verifies sensing accuracies of the terminal 1, the terminal 2, and the terminal 3. For example, the user may actually move 100 meters (m) while the pilot sensing is performed to measure the moving distance of the user. In this example, the terminal 1 measures the moving distance of the user as 110 m, the terminal 2 measures the moving distance as 105 m, and the terminal 3 measures the moving distance as 50 m. The terminal 1 compares the moving distances measured by the terminal 1, the terminal 2, and the terminal 3. Since moving distance information acquired by the terminal 3 differs from moving distance information acquired by the terminal 1 and the terminal 2, the terminal 3 determines that the sensing accuracy of the terminal 3 is relatively low.

In operation 216, the terminal 1 selects the sensing terminal for performing the sensing based on the results of the pilot sensing performed by the terminal 1, the terminal 2, and the terminal 3. In the above example, the terminal 1 selects that the moving distance measured by the terminal 3 is inaccurate and thus, does not select the terminal 3 as the sensing terminal. When a difference between the results of the pilot sensing performed by the terminal 1 and the terminal 2 is within a predetermined range, the terminal 1 selects the sensing terminal by additionally using the status information associated with the terminal 1 and the terminal 2.

As an example, when an amount of energy stored in the battery of the terminal 2 is greater than an amount of energy stored in the battery of the terminal 1, the terminal 1 selects the terminal 2 as the sensing terminal. The terminal 1 does not perform the sensing to maintain the amount of power stored in the battery of the terminal 1. When the battery level of the terminal 1 is lower than the battery level of the terminal 2, the terminal 1 selects the terminal 2 as the sensing terminal. Alternatively, a terminal 1 selects the sensing terminal based on information set by the user in advance. For example, the user sets the terminal 2 as a primary terminal for measuring the moving distance in advance. When a difference between an amount of energy stored in the battery of the terminal 1 and an amount of energy stored in the battery of the terminal 2 is within a preset range, the terminal 1 selects the terminal 2 as the sensing terminal based on the information set by the user in advance.

In operation 217, the terminal 1 selects the terminal 2 as the sensing terminal, and transmits the sensing request to the terminal 2. For example, the terminal 1 transmits a request for measuring the moving distance of the user, to the terminal 2. In operation 221, the terminal 2 performs the sensing in response to the sensing request. The terminal 2 transmits a sensing result to terminal 1, and the terminal 1 receives the sensing result in operation 218.

The terminal 1 is on standby to manage the power of the terminal 1 from a point in time of transmitting the sensing request to the terminal 2 to a point in time of receiving the sensing result. Alternatively, the terminal 1 performs sensing corresponding to the sensing performed by the sensing terminal from the point in time of transmitting the sensing request to the terminal 2 to the point in time of receiving the sensing result. For example, when the terminal 2 selected as the sensing terminal measures the moving distance of the user, the terminal 1 also measures the moving distance of the user.

The terminal 1 provides the sensing result received from the terminal 2 to the user. Also, when the terminal 1 performs the sensing corresponding to the sensing performed by the terminal 2, the terminal 1 provides a result of the sensing performed by the terminal 1 to the user. Repeated descriptions will be omitted for increased clarity and conciseness because the descriptions provided with reference to FIG. 1 are also applicable to FIG. 2.

Figure 3:
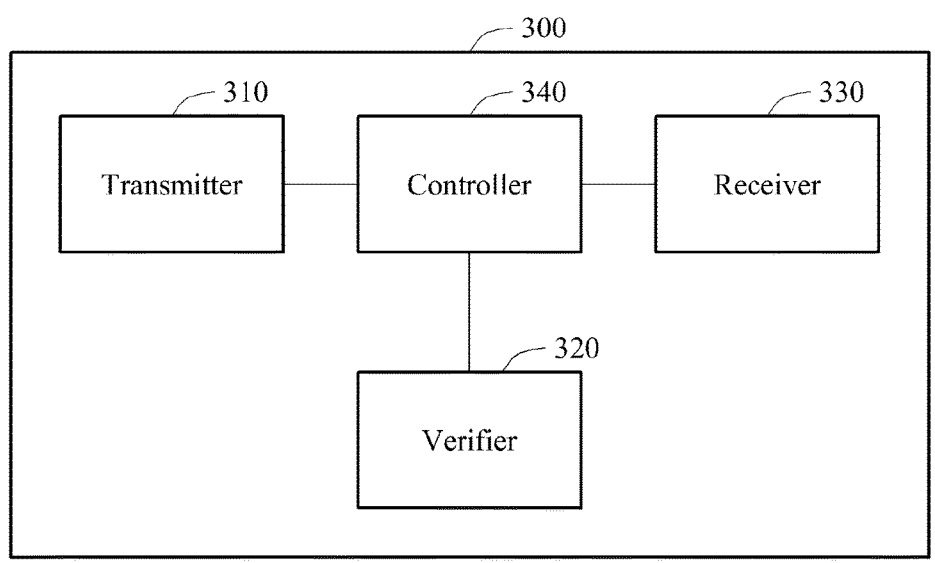
FIG. 3 is a diagram illustrating an example of a terminal for performing cooperative sensing.

FIG. 3 is a diagram illustrating a terminal for performing cooperative sensing. Referring to FIG. 3, the terminal 300 includes a transmitter 310, a verifier 320, a receiver 330, and a controller 340. Although FIG. 3 illustrates the transmitter 310, the verifier 320, the receiver 330, and the controller 340 included in the terminal 300, the transmitter 310, the verifier 320, the receiver 330, and the controller 340 may be embodied as independent hardware.

The terminal 300 receives, from a user, an execution request for a predetermined sensing function among sensing functions. In this example, the plurality of sensing functions include, for example, a function to measure a moving distance of the user, a function to measure calories used by the user, and a function to measure a heart rate of the user. However, the measured functions are not limited thereto and thus the terminal 300 may measure other functions such as blood pressure and sweat. The terminal 300 executes an application to execute the predetermined sensing function.

The transmitter 310 transmits a request to at least one cooperative terminal connected with the terminal 300, to verify a sensing performance capability of the cooperative terminal. For example, the transmitter 310 requests the cooperative terminal to perform pilot sensing to verify a sensing accuracy of the cooperative terminal with respect to the predetermined sensing function.

The verifier 320 verifies a sensing performance capability of the terminal 300. For example, the verifier 320 performs the pilot sensing to verify the sensing accuracy of the terminal 300 with respect to the predetermined sensing function.

The receiver 330 receives, from the cooperative terminal, first capability information generated in response to the request transmitted to verify the sensing performance capability of the cooperative terminal.

The controller 340 selects a sensing terminal for performing sensing based on at least one of the first capability information and second capability information generated by verifying the sensing performance capability of the terminal 300. The controller 340 selects the sensing terminal for performing the predetermined sensing function based on at least one of the first capability information and the second capability information. The sensing corresponds to an execution request for the predetermined sensing function from the user. For example, when the user inputs an execution request for the function to measure the moving distance to the terminal 300, the sensing terminal performs sensing by measuring the moving distance of the user. Pilot sensing information acquired by the terminal 200 is a measured value of a sensor in the terminal 300. The controller 340 verifies a sensing accuracy of the terminal 300, and verifies a sensing accuracy of the cooperative terminal.

The controller 340 verifies the sensing accuracies of the terminal and the cooperative terminal based on the first capability information and the second capability information. Based on a result of the verifying, the controller 340 selects a device having a higher sensing accuracy than the sensing terminal. The controller 340 selects the sensing terminal by additionally using status information associated with the terminal 300 and the cooperative terminal. In this example, the status information associated with the terminal 300 and the cooperative terminal is one of information on sensors included in the terminal 300 and the cooperative terminal, battery information associated with the terminal 300 and the cooperative terminal, an amount of power used for the sensing performed by the terminal and the cooperative terminal, and user preference information with respect to the sensing terminal.

When a difference between the verified sensing accuracies is within a reference range, the controller 340 selects the sensing terminal based on the battery information associated with the terminal 300 and the cooperative terminal. The controller 340 selects, as the sensing terminal, a device including a battery storing a greater amount of energy. In response to the selecting, power of devices included in a network is managed.

When the difference between the verified sensing accuracies is within the reference range, the controller 340 selects the sensing terminal based on the user preference information with respect to the sensing terminal. The user sets a device for preferentially performing a predetermined function, among the plurality of devices included in a network. For example, between the terminal 300 and a wearable device, the user sets the wearable device as a device for performing the function to measure the moving distance. The user preference information is generated based on a result of the setting. The user preference information is shared in the network.

In an example, the terminal 300 selects the cooperative terminal as the sensing terminal. When the cooperative terminal is selected as the sensing terminal, the transmitter 310 transmits the sensing request to the cooperative terminal to perform the sensing. Also, the receiver 330 receives the sensing information acquired by performing the sensing from the cooperative terminal. The terminal 300 further includes an output unit. The output unit outputs the sensing information based on at least one of the visual scheme, the auditory scheme, and the tactile scheme.

In an example, from neighboring terminals connected with the terminal 300, the terminal 300 selects a cooperative terminal for performing the pilot sensing based on status information associated with the neighboring terminals. The terminal 300 and the plurality of neighboring terminals share the status information in the network. In this example, the status information is one of information on a sensor included in each of the neighboring terminals, battery information for each of the neighboring terminals, and an amount of power used for the pilot sensing performed by each of the neighboring terminals. Repeated descriptions will be omitted for increased clarity and conciseness because the descriptions provided with reference to FIGS. 1 and 2 are also applicable to each block illustrated in FIG. 3.

FIGS. 4 through 7 are diagrams illustrating examples of cooperative sensing.

Figure 4:
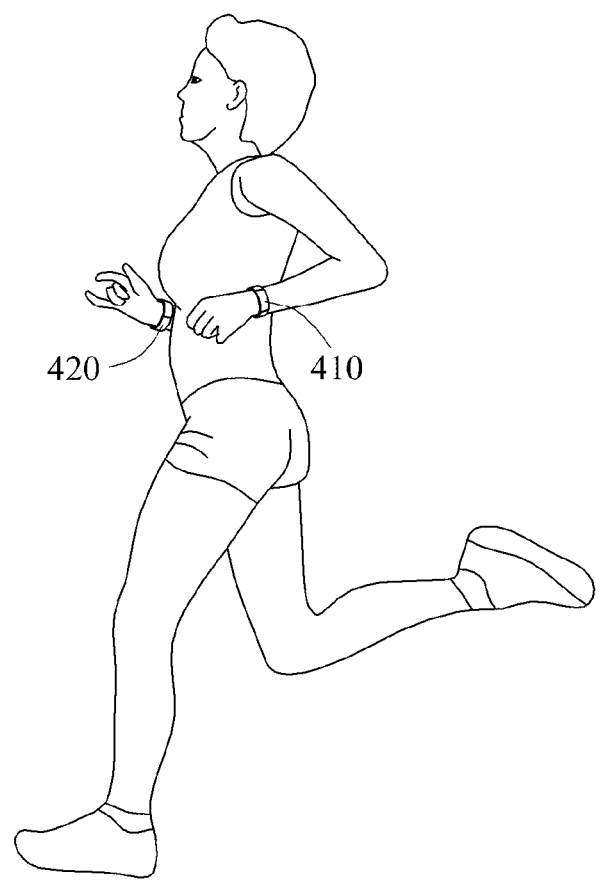
FIGS. 4 through 7 are diagrams illustrating examples of cooperative sensing.

Referring to FIG. 4, a user wears wearable devices, for example, wearable devices 410 and 420. The wearable devices 410 and 420 are connected in a WLAN but is not limited thereto. For example, the wearable devices 410 and 420 may be connected using a WiFi direct, a DLNA, a WiBro, a WiMAX, an HSDPA, a Bluetooth™ module, an RFID tag, an IrDA, a UWB, a ZigBee, and an NFC. The wearable devices 410 and 420 may share status information. The wearable device 410 verifies status information associated with the wearable device 420, and the wearable device 420 verifies status information associated with the wearable device 410.

The user executes a calorie consumption measurement application stored in the wearable device 410. In response to an execution of the calorie consumption measurement application, the wearable device 410 transmits a request to the wearable device 420 to verify a calorie consumption measurement capability of the wearable device 420. As an example, the wearable device 410 requests the wearable device 420 to perform pilot sensing to verify a measurement accuracy for the calorie consumption measurement capability.

In an example, the wearable device 420 determines whether the wearable device 420 is capable of performing the pilot sensing. The wearable device 420 determines whether the wearable device 420 is capable of performing the pilot sensing based on battery information and whether a sensor for measuring calorie consumption is present.

The wearable device 420 performs the pilot sensing to verify the measurement accuracy for the calorie consumption in response to the request. The wearable device 420 acquires information on the calorie consumption of the user using an acceleration sensor. The wearable device 420 transmits the acquired information to the wearable device 410. Alternatively, in response to the request, the wearable device 420 provides a notification to the wearable device 410 indicating that the wearable device 420 is incapable of measuring the calorie consumption.

The wearable device 410 verifies a calorie consumption measurement capability of the wearable device 410. As an example, the wearable device 410 performs the pilot sensing to verify a measurement accuracy for the calorie measurement capability. The wearable device 410 acquires information on the calorie consumption of the user using the acceleration sensor. Alternatively, the wearable device 410 verifies that the wearable device 410 is incapable of measuring the calorie consumption.

When the wearable devices 410 and 420 are capable of measuring the calorie consumption, the wearable device 410 compare information acquired by the wearable device 410 and information acquired by the wearable device 420. For example, when the information acquired by the wearable device 410 indicates 500 calories and the information acquired by the wearable device 420 indicates 490 calories, the wearable device 410 determines that the measurement accuracy of the wearable device 410 is similar to the measurement accuracy of the wearable device 420.

When the measurement accuracies of the wearable devices 410 and 420 are similar to one another, the wearable device 410 selects a sensing terminal for measuring the calorie consumption of the user based on the battery information for each of the wearable devices 410 and 420. For example, when an amount of energy stored in a battery of the wearable device 420 is greater than an amount of energy stored in a battery of the wearable device 410, the wearable device 410 selects the wearable device 420 as the sensing terminal.

The wearable device 420 selected as the sensing terminal measures the calorie consumption of the user. The wearable device 410 receives a sensing result from the wearable device 420, and displays the calorie consumption of the user on a display.

Figure 5:
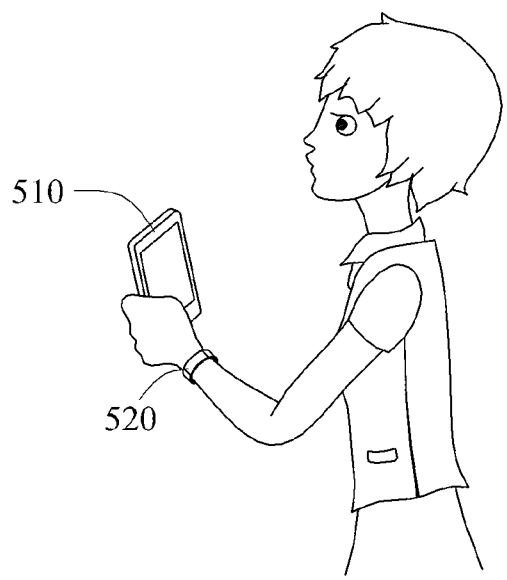

Referring to FIG. 5, a user wears a wearable device 520 on a wrist and holds a mobile terminal 510 using a hand. A camera of the mobile terminal 510 and the wearable device 520 are used to measure a heart rate of the user but is not limited thereto. For example, the wearable device 520 and the mobile terminal 510 may be used to measure a walking or moving distance of the user. Information recognized by the camera of the mobile terminal 510 varies based on an environment of the mobile terminal 510. When a brightness of the environment is relatively high, the camera of the mobile terminal 510 accurately recognizes the user and the environment. When a brightness of the environment is relatively low, the camera of the mobile terminal 510 inaccurately recognizes the user and the environment.

The mobile terminal 510 receives an execution request for a heart rate measuring function from the user. In response to the execution request from the user, the mobile terminal 510 executes a heart rate measurement application. In response to an execution of the heart rate measurement application, the mobile terminal 510 requests the wearable device 520 to perform pilot sensing. The wearable device 520 acquires heart rate information associated with the user during a relatively short period of time by performing the pilot sensing. Also, the mobile terminal 510 acquires heart rate information associated with the user during a relatively short period of time through the pilot sensing.

The wearable device 520 transmits a result of the pilot sensing to the mobile terminal 510. The mobile terminal 510 compares the heart rate information acquired by the mobile terminal 510 and the heart rate information acquired by the wearable device 520. When a brightness of the environment is relatively low, the camera of the mobile terminal fails to accurately acquire the heart rate information. When a brightness of the environment is relatively low, the heart rate information acquired by the wearable device 520 is more accurate than the heart rate information acquired by the mobile terminal 510. Based on the result of the pilot sensing, the mobile terminal 510 selects a device for measuring a heart rate more accurately.

The mobile terminal 510 selects the wearable device 520 as a sensing terminal. The wearable device 520 measures the heart rate of the user by performing a sensing, and transmitting a measurement result to the mobile terminal 510. The mobile terminal 510 displays the measurement result on a display.

Figure 6:
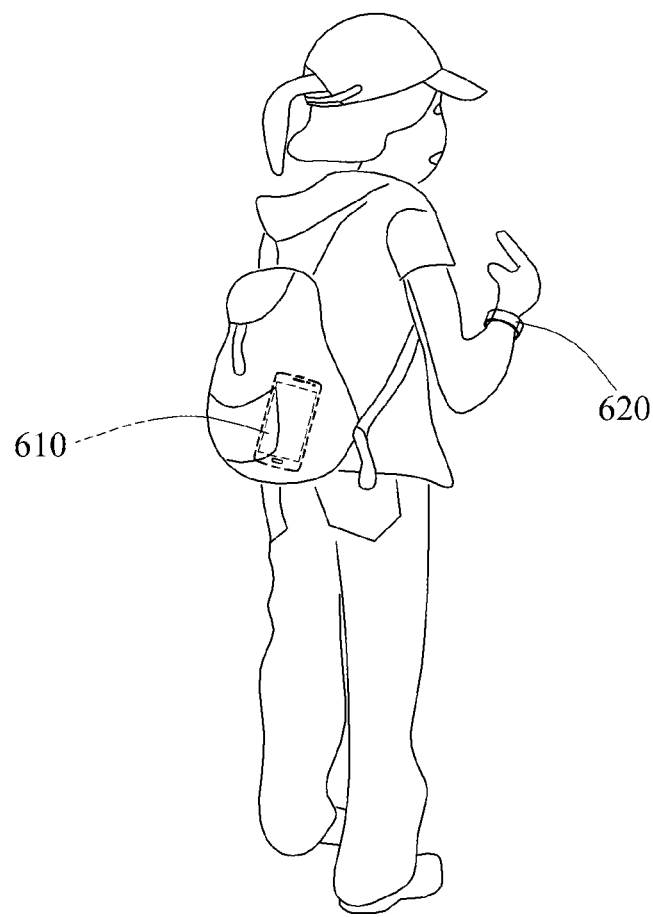

Referring to FIG. 6, a mobile terminal 610 is disposed in a backpack of a user, and a wearable device 620 is disposed on a wrist of the user. The mobile terminal 610 is capable of measuring a moving distance of the user while the wearable device 620 is incapable of measuring the moving distance. In various situations, the wearable device 620 is incapable of measuring the moving distance. As an example, when a sensor of the wearable device 620 is in an inoperable state due to, for example, a defect of the sensor, the wearable device 620 is incapable of measuring the moving distance. Conversely, when a sensor for measuring the moving distance is not included in the wearable device 620, the wearable device 620 is incapable of measuring the moving distance.

The user takes the mobile terminal 610 out of the backpack to measure the moving distance. Also, the user requests the mobile terminal 610 to perform a function to measure the moving distance using the wearable device 620 in lieu of taking out the mobile terminal 610. The wearable device 620 executes a moving distance measurement application stored in the wearable device 620 in response to the request from the user. In response to the executing, the wearable device 620 requests the mobile terminal 610 to perform pilot sensing. The mobile terminal 610 performs the pilot sensing using, for example, a GPS sensor and transmits, to the wearable device 620, moving distance information acquired during a relatively short period of time through the pilot sensing.

As described above, the wearable device 620 is incapable of measuring the moving distance of the user. The wearable device 620 selects the mobile terminal 610 as a sensing terminal. The wearable device 620 requests the mobile terminal 610 selected as the sensing terminal, to perform sensing.

In response to the request from the wearable device 62, the mobile terminal 610 measures the moving distance of the user, and transmits a measurement result to the wearable device 620. The wearable device 620 displays the measurement result on a display. The user conveniently verifies the moving distance without taking out the mobile terminal 610.

In contrast to the preceding example, the mobile terminal 610 and the wearable device 620 are capable of measuring the moving distance. The mobile terminal 610 and the wearable device 620 use different sensors to acquire the moving distance information. For example, the mobile terminal 610 includes a GPS sensor, and the wearable device 620 includes an acceleration sensor. The user sets a primary device to be used for measuring the moving distance using the moving distance measurement application. User preference information is stored by setting the primary device.

When a pilot sensing result indicates that accuracies of the moving distance information acquired by the mobile terminal 610 and the wearable device 620 during a relatively short period of time are similar, the wearable device 620 selects the sensing terminal based on a result of the setting. When the user sets the wearable device 620 as the primary device, the wearable device 620 is selected as the sensing terminal.

Figure 7:
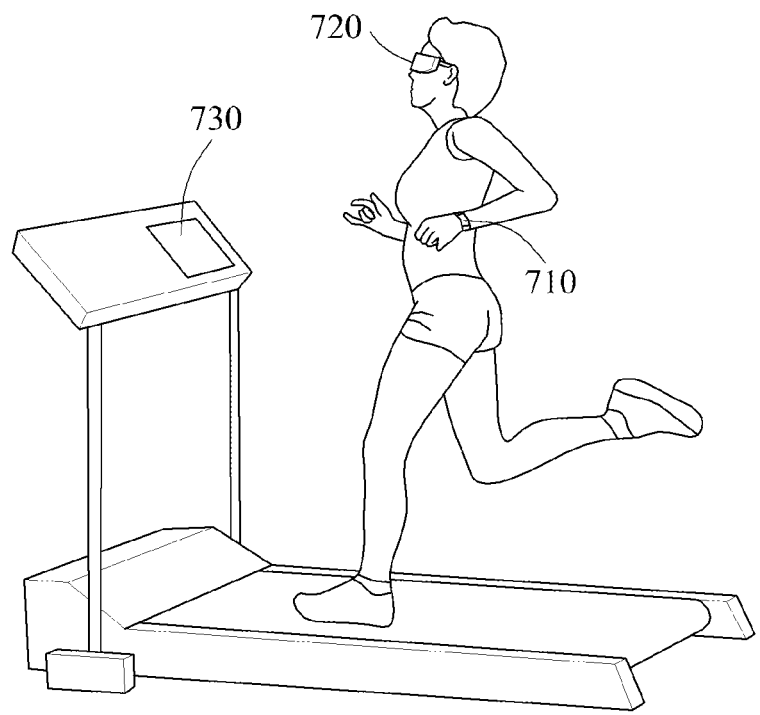

Referring to FIG. 7, a user exercises using gym equipment in an indoor region. The user wears wearable devices, for example, wearable devices 710 and 720, and a mobile terminal 730 of the user is disposed on the gym equipment. The mobile terminal 730 disposed on the gym equipment and the wearable devices 710 and 720 are connected to one another. For example, the mobile terminal 730 and the wearable devices 710 and 720 may form a WBAN corresponding to a low power network. In lieu of the WBAN, the mobile terminal 730 and the wearable devices 710 and 720 may form, for example, a WLAN, a WiFi direct, a DLNA, a WiBro, a WiMAX, an HSDPA, a Bluetooth™ module, an RFID tag, an IrDA, a UWB, a ZigBee, and an NFC.

The user executes a calorie consumption measurement application stored in the wearable device 710 to measure calorie consumption. In response to the executing, the wearable device 710 transmits a request to the wearable device 720 and the mobile terminal 730 to verify a calorie consumption measurement capability.

The wearable device 710 verifies whether the wearable device 710 is capable of measuring the calorie consumption. For example, the wearable device 710 verifies whether the wearable device 710 is capable of measuring the calorie consumption based on at least one of battery information, whether a sensor for measuring the calorie consumption is present, and whether the sensor is in an operable state. To perform the verifying, the wearable device 710 performs pilot sensing.

The wearable device 720 transmits, to the wearable device 710, a message indicating that the wearable device 720 is incapable of measuring the calorie consumption. In response to the request, the mobile terminal 730 performs pilot sensing, and transmits a result of the pilot sensing to the wearable device 710. In this example, as described above, the pilot sensing is performed to verify a sensing accuracy on the calorie consumption measurement capability.

The wearable device 710 selects a sensing terminal for measuring the calorie consumption based on a result of the pilot sensing performed by the wearable device 710 and a result of the pilot sensing transmitted from the mobile terminal 730. In a case in which the user exercises while carrying the mobile terminal 730, the mobile terminal 730 measures the calorie consumption by sensing a movement of the user. When the mobile terminal 730 is disposed on the gym equipment as illustrated in FIG. 7, the mobile terminal 730 inaccurately senses the movement of the user. In this example, the mobile terminal 730 inaccurately measures the calorie consumption of the user and thus, the calorie consumption measured by the mobile terminal 730 through the pilot sensing during a relatively short period of time is inaccurate.

The wearable device 710 selects a device providing higher calorie consumption measurement accuracy, as the sensing terminal from between the wearable device 710 and the mobile terminal 730, and selects the wearable device 710 as the sensing terminal.

Although cooperative sensing performed by two or three apparatuses is described with reference to FIGS. 4 through 7, it will be apparent to those skilled in the art that the cooperative sensing is also be performed by four or more apparatuses.

The descriptions provided with reference to FIGS. 1 through 3 are applicable to the descriptions provided with reference to FIGS. 4 through 7. Also, the descriptions provided with reference to FIGS. 4 through 7 are applicable to the descriptions provided with reference to FIGS. 1 through 3 and repeated descriptions shall be omitted for brevity.

Figure 8:
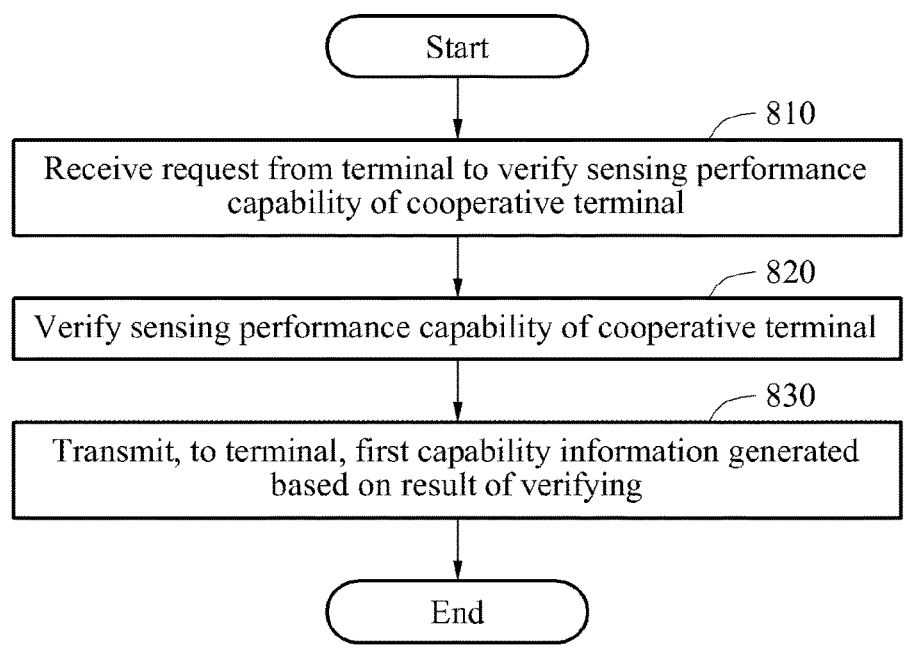
FIG. 8 is a flowchart illustrating an example of a cooperative sensing method of a cooperative terminal.

FIG. 8 is a flowchart illustrating an example of cooperative sensing method of a cooperative terminal.

Referring to FIG. 8, in operation 810, the cooperative terminal receives a request from a terminal to verify a sensing performance capability of the cooperative terminal. The cooperative terminal is a mobile device physically distinguished from the terminal. The terminal receives an execution request for a predetermined sensing function, for example, a function to measure calorie consumption, from a user.

The cooperative terminal is connected to the terminal. For example, the cooperative terminal and the terminal form a WBAN corresponding to a low power network. In lieu of the WBAN, the cooperative terminal is connected to the terminal through, for example, a WLAN, a WiFi direct, a DLNA, a WiBro, a WiMAX, an HSDPA, a Bluetooth™ module, an RFID tag, an IrDA, a UWB, a ZigBee, and an NFC.

In operation 820, the cooperative terminal verifies the sensing performance capability of the cooperative terminal. For example, the cooperative terminal performs pilot sensing to verify a sensing accuracy on the predetermined sensing function. In this example, the terminal verifies a sensing performance capability of the terminal.

In operation 830, the cooperative terminal transmits first capability information generated based on a result of the verifying, to the terminal. For example, when the cooperative terminal performs the pilot sensing to verify the sensing accuracy on the predetermined sensing function, the cooperative terminal generates pilot sensing information on the pilot sensing, and transmits the pilot sensing information to the terminal. As another example, the cooperative terminal determines that the cooperative terminal is incapable of performing the predetermined sensing function, and provides notification indicting that the cooperative terminal is incapable of performing the predetermined sensing function, to the terminal.

The terminal selects a sensing terminal for performing the predetermined sensing function based on at least one of the first capability information received from the cooperative terminal and second capability information generated by verifying the sensing performance capability of the terminal.

Also, the terminal selects the sensing terminal by additionally using status information associated with the terminal and the cooperative terminal. In this example, the status information associated with the terminal and the cooperative terminal include one of information on sensors included in the terminal and the cooperative terminal, battery information associated with the terminal and the cooperative terminal, an amount of power to be used for sensing performed by the terminal and the cooperative terminal, and user preference information with respect to the sensing terminal.

Repeated descriptions will be omitted for increased clarity and conciseness because the descriptions provided with reference to FIGS. 1 through 7 are also applicable to each block of FIG. 8.

Figure 9:
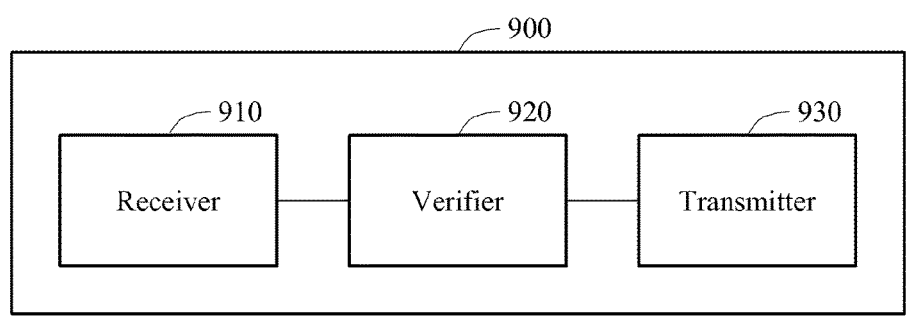
FIG. 9 is a diagram illustrating an example of a cooperative terminal for performing cooperative sensing.

FIG. 9 is a diagram illustrating a cooperative terminal for performing cooperative sensing.

Referring to FIG. 9, the cooperative terminal 900 includes a receiver 910, a verifier 920, and a transmitter 930. Although FIG. 9 illustrates the receiver 910, the verifier 920, and the transmitter 930 as being included in the cooperative terminal 900, the receiver 910, the verifier 920, and the transmitter 930 may be embedded as independent hardware and thus the cooperative terminal 900 may include more or less elements.

The receiver 910 receives a request from a terminal to verify a sensing performance capability of the cooperative terminal 900.

The verifier 920 verifies the sensing performance capability of the cooperative terminal 900. For example, the verifier 920 performs pilot sensing to verify a sensing accuracy of the cooperative terminal 900 with respect to a predetermined sensing function.

The transmitter 930 transmits first capability information generated based on a result of the verifying, to the terminal. For example, when the cooperative terminal 900 performs the pilot sensing, the transmitter 930 transmits, to the terminal, pilot sensing information acquired by performing the pilot sensing. Also, when the verifier 920 verifies that the cooperative terminal 900 lacks the sensing performance capability corresponding to the execution request for the predetermined sensing function received by the terminal, the transmitter 930 provides notification indicating that the cooperative terminal 900 is incapable of performing the predetermined sensing function, to the terminal.

The terminal selects a sensing terminal for performing sensing, based on one of the first capability information received from the cooperative terminal 900 and second capability information generated by verifying the sensing performance capability of the terminal. The sensing terminal is selected from between the terminal and the cooperative terminal 900 based on information collected and received by the terminal.

Since the descriptions provided with reference to FIGS. 1 through 7 are also applicable to each block of FIG. 9, repeated descriptions will be omitted for increased clarity and conciseness.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skilled in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A cooperative sensing method of a terminal, the method comprising:
    generating a first biometric information of a user by performing a first pilot sensing using a sensor of the terminal;
    transmitting, to another terminal, a request to perform a second pilot sensing;
    receiving, from the other terminal, a second biometric information of the user generated by the other terminal performing the second pilot sensing using a sensor of the other terminal;
    comparing the first biometric information of the user with the second biometric information of the user;
    transmitting a request to perform sensing to the other terminal based on a result of the comparing; and
    receiving, from the other terminal, a third biometric information of the user generated by the other terminal performing the sensing.

2. The method of claim 1, wherein:
    the transmitting of the request to perform the second pilot sensing comprises requesting the other terminal to perform the second pilot sensing to verify a sensing accuracy of the other terminal, and
    the performing of the first pilot sensing comprises performing the first pilot sensing to verify a sensing accuracy of the terminal.

3. The method of claim 1, further comprising:
    selecting, by the terminal, the other terminal as a sensing terminal based on status information associated with the terminal and the other terminal,
    wherein the transmitting of the sensing request comprises transmitting the sensing request to the other terminal in response to the other terminal being selected as the sensing terminal.

4. The method of claim 3, wherein the status information comprises any one or any combination of any two or more of information on sensors included in the terminal and the other terminal, battery information of the terminal and the other terminal, an amount of power used for sensing performed by each of the terminal and the other terminal, and individual preference information associated with the sensing terminal.

5. The method of claim 1, further comprising:
    selecting, by the terminal, the other terminal as a sensing terminal based on battery information of the terminal and the other terminal in response to a difference between verified sensing accuracies of the terminal and the other terminal being within a reference range,
    wherein the transmitting of the sensing request comprises transmitting the sensing request to the other terminal in response to the other terminal being selected as the sensing terminal.

6. The method of claim 1, further comprising:
    selecting, by the terminal, the other terminal as a sensing terminal based on individual preference information associated with the terminal and the other terminal, respectively, in response to a difference between verified sensing accuracies of the terminal and the other terminal being within a reference range,
    wherein the transmitting of the sensing request comprises transmitting the sensing request to the other terminal in response to the other terminal being selected as the sensing terminal.

7. The method of claim 1, further comprising:
    outputting the biometric information based on any one or any combination of any two or more of a visual scheme, an auditory scheme, and a tactile scheme,
    wherein the transmitting of the sensing request comprises transmitting the sensing request to the other terminal in response to the other terminal being selected as a sensing terminal.

8. The method of claim 1, further comprising:
    selecting, from among neighboring terminals, the other terminal to perform the pilot sensing based on status information associated with the neighboring terminals.

9. The method of claim 8, wherein the status information comprises any one or any combination of any two or more of information on a sensor included in each of the neighboring terminals, battery information for each of the neighboring terminals, and an amount of power used for pilot sensing performed by each of the neighboring terminals.

10. The method of claim 2, wherein the sensing accuracy of the terminal and the sensing accuracy of the other terminal are determined based on an environment of the terminal and the other terminal, respectively.

11. A terminal for performing cooperative sensing, the terminal comprising:
    a sensor configured to generate a first biometric information of a user by performing a first initial sensing;
    a transmitter configured to transmit, to a cooperative terminal, a request to perform a second initial sensing;
    a receiver configured to receive, from the cooperative terminal, a second biometric information of the user generated by the cooperative terminal performing the second pilot sensing using a sensor of the cooperative terminal; and
    a controller configured to:
        compare the first biometric information of the user with the second biometric information of the user, and select either one or both of the terminal and the cooperative terminal as a sensing terminal based on a result of the comparing, wherein the transmitter is further configured to transmit a request to perform sensing to the cooperative terminal in response to the cooperative terminal being selected as the sensing terminal, and wherein the receiver is further configured to receiver, from the cooperative terminal, a third biometric information of the user generated by the cooperative terminal performing the sensing.

12. The terminal of claim 11, wherein the transmitter is further configured to request the cooperative terminal to perform the second pilot sensing to verify a sensing accuracy of the cooperative terminal, and the sensor is further configured to perform the first pilot sensing to verify a sensing accuracy of the terminal.

13. The terminal of claim 11, wherein the controller is further configured to select the sensing terminal using status information associated with the terminal and the cooperative terminal.

14. The terminal of claim 13, wherein the status information comprises any one or any combination of any two or more of information on sensors included in the terminal and the cooperative terminal, battery information associated with the terminal and the cooperative terminal, an amount of power used for sensing performed by each of the terminal and the cooperative terminal, and individual preference information associated with the sensing terminal.

15. The terminal of claim 11, wherein the controller is further configured to select either one or both of the terminal and the cooperative terminal as the sensing terminal based on battery information of the terminal and the cooperative terminal in response to a difference between the first biometric information of the user with the second biometric information of the user being within a reference range.

16. A cooperative terminal configured to perform cooperative sensing, the cooperative terminal comprising:

a receiver configured to receive, from a terminal, a request;

a sensor configured to, in response to the request, generate a first biometric information of a user by performing the initial sensing;

a verifier configured to verify the sensing performance capability of the cooperative terminal based on and to generate capability information of the cooperative terminal based on the generated biometric information of the user; and a transmitter configured to transmit, to the terminal, the capability information of the cooperative terminal, wherein the terminal is configured to select either one or both of the device and the cooperative device as a sensing terminal to perform sensing based on either one or both of the capability information of the cooperative terminal and capability information of the terminal, and wherein the sensor is further configured to generate a second biometric information of the user by performing the sensing, in response to the cooperative terminal being selected as the sensing terminal.

17. The cooperative terminal of claim 16, wherein the verifier is configured to verify a sensing accuracy of the cooperative terminal with respect to a predetermined sensing function, based on the generated first biometric information of the user.

18. The cooperative terminal of claim 17, wherein the transmitter is further configured to transmit, to the terminal, the generated first biometric information of the user.

19. The cooperative terminal of claim 16, wherein the transmitter is configured to provide a notification to the terminal indicating that the cooperative terminal is incapable of performing the initial sensing, in response to the verifier verifying that the cooperative terminal lacks the sensing performance capability for-a performing the initial sensing.

20. A non-transitory computer-readable storage medium storing instructions that, when executed by a processing device, cause the processing device to perform the method of claim 1.

* * * * *